United States Patent
Guala

(10) Patent No.: US 8,348,928 B2
(45) Date of Patent: Jan. 8, 2013

(54) FLOW COMPONENT FOR MEDICAL INFUSION/TRANSFUSION LINES

(75) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 554 days.

(21) Appl. No.: 12/146,556

(22) Filed: Jun. 26, 2008

(65) Prior Publication Data

US 2009/0005761 A1    Jan. 1, 2009

(30) Foreign Application Priority Data

Jun. 29, 2007  (IT) .............................. TO2007A0473

(51) Int. Cl.
| | |
|---|---|
| A61M 25/16 | (2006.01) |
| A61M 25/18 | (2006.01) |
| A61M 5/00 | (2006.01) |
| A61M 5/14 | (2006.01) |
| A61M 39/00 | (2006.01) |
| A61M 39/10 | (2006.01) |
| A61M 39/02 | (2006.01) |
| A61M 25/00 | (2006.01) |

(52) U.S. Cl. ........ 604/537; 128/912; 604/246; 604/256; 604/533; 604/534; 604/535; 604/539; 604/284

(58) Field of Classification Search ............... 128/912; 222/563; 251/149.3, 335.1, 335.2, 356, 359, 251/360, 363; 604/164.01, 164.02, 167.01, 604/167.02, 167.03, 167.04, 167.06, 246, 604/247, 256, 284, 533, 534, 535, 537, 539, 604/905, 93.01, 30, 48, 236, 237, 238, 536

See application file for complete search history.

(56) References Cited

U.S. PATENT DOCUMENTS

| | | | | |
|---|---|---|---|---|
| 5,171,234 | A | * | 12/1992 | Jepson et al. ................. 604/534 |
| 5,242,413 | A | * | 9/1993 | Heiliger .................... 604/167.04 |
| 5,400,500 | A | | 3/1995 | Behnke et al. |
| 5,501,426 | A | * | 3/1996 | Atkinson et al. ............ 251/149.1 |
| 6,165,168 | A | * | 12/2000 | Russo ............................ 604/533 |
| 6,254,529 | B1 | * | 7/2001 | Ouchi ........................... 600/154 |
| 6,723,073 | B2 | * | 4/2004 | Ley et al. ................. 604/167.01 |
| 7,011,314 | B2 | * | 3/2006 | McFarlane .................... 277/626 |
| 2002/0091359 | A1 | * | 7/2002 | Caleffi ..................... 604/167.04 |
| 2005/0256460 | A1 | * | 11/2005 | Rome et al. ................... 604/247 |
| 2006/0111694 | A1 | * | 5/2006 | Fukai et al. ................... 604/905 |
| 2006/0167411 | A1 | * | 7/2006 | Weston et al. ................. 604/110 |

FOREIGN PATENT DOCUMENTS

| | | |
|---|---|---|
| JP | 2004 195181 A | 7/2004 |
| JP | 2004 275665 A | 10/2004 |

OTHER PUBLICATIONS

European Search Report for corresponding EP Application No. EP08158708.1, dated Nov. 17, 2008.

* cited by examiner

*Primary Examiner* — Kevin C Sirmons
*Assistant Examiner* — Shefali Patel
(74) *Attorney, Agent, or Firm* — Heslin Rothenberg Farley & Mesiti P.C.; Victor A. Cardona, Esq.

(57) ABSTRACT

A flow component for medical infusion/transfusion lines includes a tubular body having a side inlet connector, housed in a fluid-tight way in which is an elastic sealing element that can be traversed by a fluid introducer. The elastic sealing element has at least one axial cavity, which defines, for traversal by the fluid introducer, a diaphragm of small thickness.

7 Claims, 4 Drawing Sheets

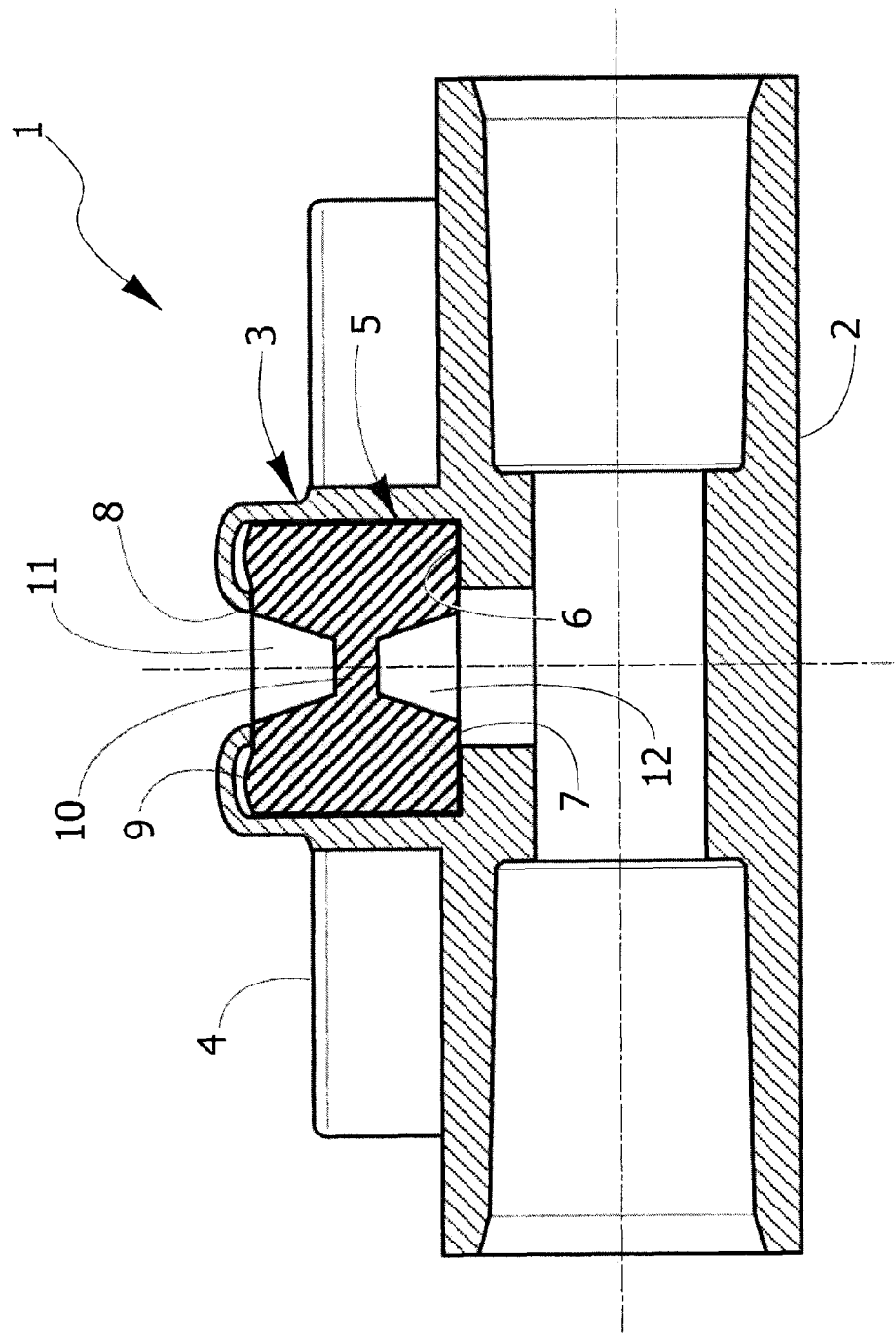

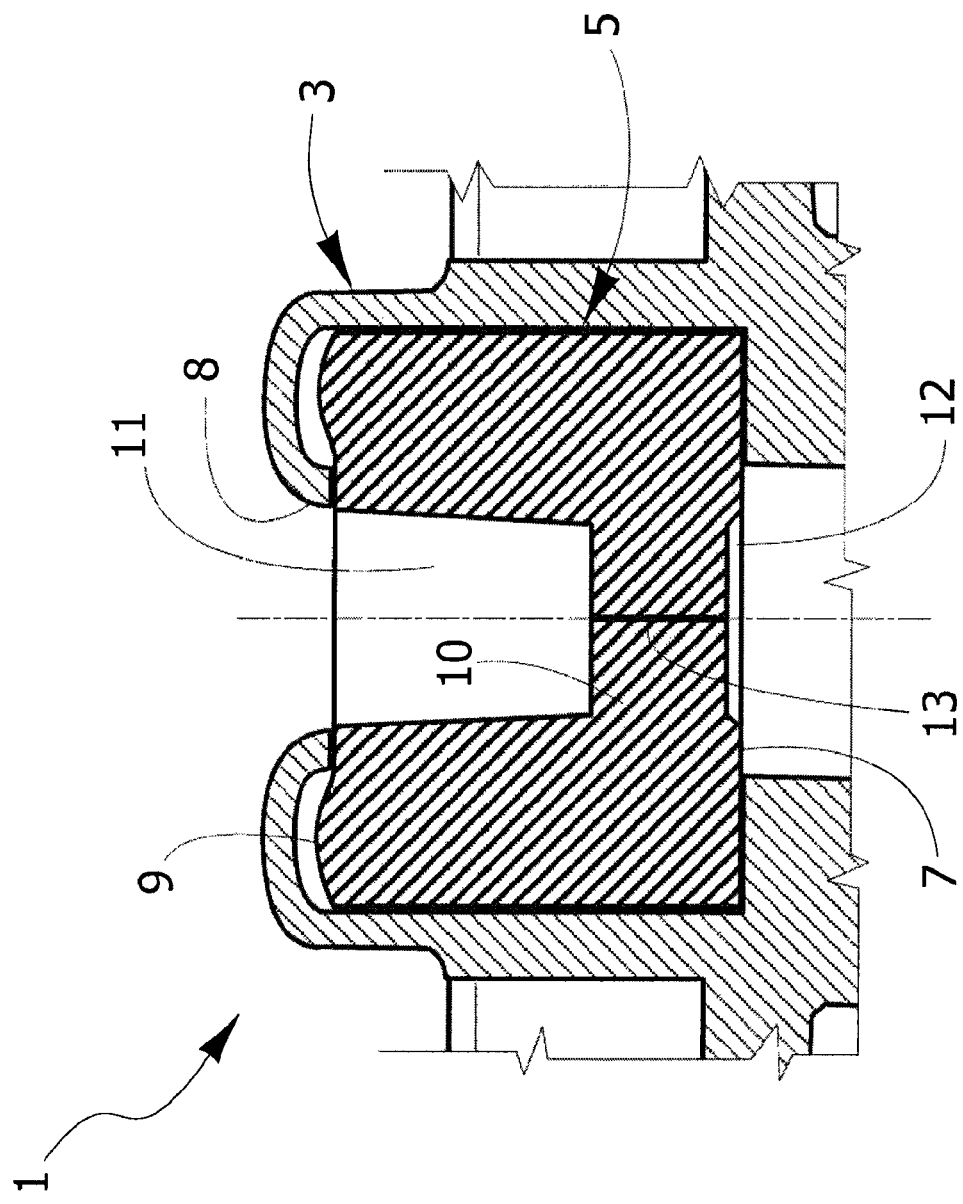

FLOW COMPONENT FOR MEDICAL INFUSION/TRANSFUSION LINES

CROSS-REFERENCE TO RELATED APPLICATIONS

This application claims priority from Italian patent application Serial No. TO2007A000473, filed on Jun. 29, 2007, the entirety of which is hereby incorporated by reference.

FIELD OF THE INVENTION

The present invention relates in general to medical infusion/transfusion lines. More in particular, the subject of the invention is a flow component for medical lines of this sort, which comprises a tubular body having a side inlet connector, within which a fluid introducer can be inserted and which houses in a fluid-tight way an elastic sealing element that can be traversed by the fluid introducer.

STATE OF THE PRIOR ART

In a typical embodiment of a flow component of this type, the tubular body has a general T-shaped or cross-shaped conformation, with a main duct for a primary fluid, converging radially into which is the inlet connector, along with the corresponding elastic sealing element.

The above elastic sealing element traditionally consists of a body made of elastomeric material, axially blocked at its ends between two annular arrests, one axially external and the other axially internal, of the inlet connector. The elastic sealing element typically has a generally cylindrical shape, with an axial dimension substantially corresponding to that of the inlet connector, normally in the region of 6 mm and more. Equally typically, the fluid introducer used with flow components of the above sort is constituted by the thin tubular needle of an injection syringe.

In use, the perforation of the elastic sealing element and its traversal by the needle of the fluid introducer is inconvenient, in so far as it requires the operator to exert a certain amount of effort, and also involves the risk of the needle, on the tip of which a certain load is applied, possibly undergoing flexure until it bends or even breaks, instead of perforating the elastic sealing element. This risk is particularly high in the case where the needle of the fluid introducer is pushed by the operator against the elastic sealing element, instead of in a position where it is properly centred and aligned with its axis, in an off-centre condition and/or with a more or less accentuated angle with respect to the axis of the inlet connector. In such an eventuality, the tip of the needle, instead of traversing the elastic sealing element completely, can intercept the wall of the inlet connector, thus preventing proper injection of fluid by the introducer to the main duct of the flow component.

SUMMARY OF THE INVENTION

The object of the present invention is to overcome the aforesaid drawbacks, and said object is achieved by means of a flow component of the type defined at the start, basically characterized in that the aforesaid elastic sealing element has, at least on the side of the external annular arrest of the inlet connector, an axial cavity that defines, for traversal by said fluid introducer, a diaphragm of small thickness.

Thanks to this arrangement, traversal of the elastic sealing element by the fluid introducer requires, in use, an appreciably smaller amount of effort on the part of the operator, without on the other hand affecting in any way the features of sealing of the inlet connector by the elastic element. Furthermore, the axial cavity of the elastic sealing element facilitates centering of the fluid introducer, thus favouring proper traversal of the diaphragm of small thickness of the elastic element and reducing the risk of said introducer erroneously intercepting the wall of the inlet connector, thus getting stuck.

This additional advantage can be further accentuated in the case where, according to a preferred embodiment of the invention, the aforesaid cavity has a conical side surface converging towards the aforesaid diaphragm of small thickness.

According to another advantageous characteristic of the invention, the elastic sealing element has, on the side of the internal axial arrest of the inlet connector, a second axial cavity, and the diaphragm of small thickness is set in a median area of said elastic sealing element comprised between said cavities.

This characteristic facilitates assembly of the flow component, given that the elastic sealing element has in this case a symmetrical conformation that enables insertion and locking thereof within the inlet connector indifferently in a first position or else in a second position turned over through 180°.

In a variant of the invention, in which the flow component can be used with a fluid introducer without needle, the diaphragm of small thickness of the elastic sealing element has a pre-slit, and the cavity that defines said diaphragm has a conformation like a female Luer cone.

BRIEF DESCRIPTION OF THE DRAWINGS

Further characteristics and advantages of the invention will emerge clearly in the course of the ensuing detailed description, with reference to the annexed drawings, which are provided purely by way of non-limiting example and in which:

FIG. 3 is a longitudinal sectional view at a larger scale of the embodiment of FIG. 1; and FIG. 4 is a partial view similar to that of FIG. 3 illustrating a second example of embodiment of the flow component according to the invention.

DETAILED DESCRIPTION OF THE INVENTION

Figure 1:
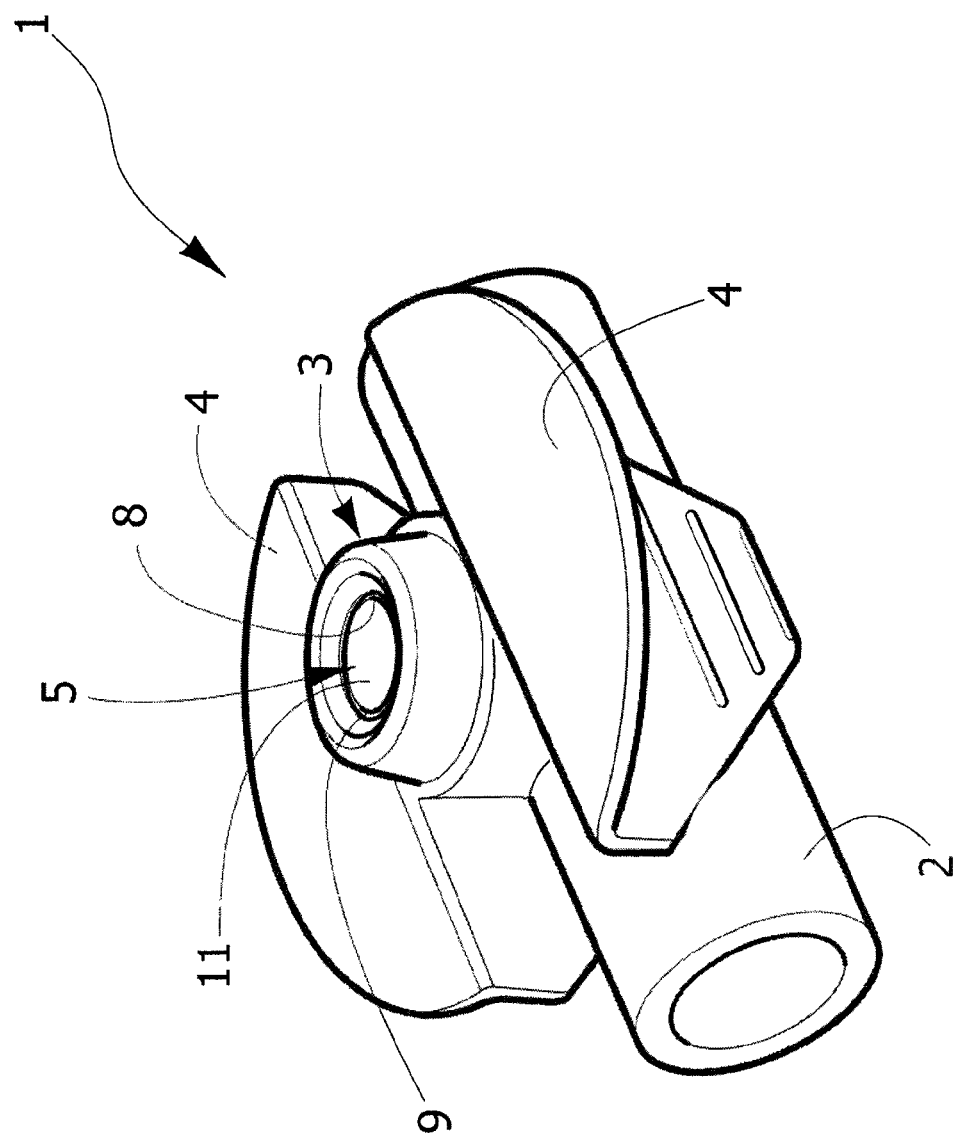
FIG. 1 is a schematic perspective view of a first example of embodiment of a flow component according to the invention for medical infusion/transfusion lines.
Figure 2:
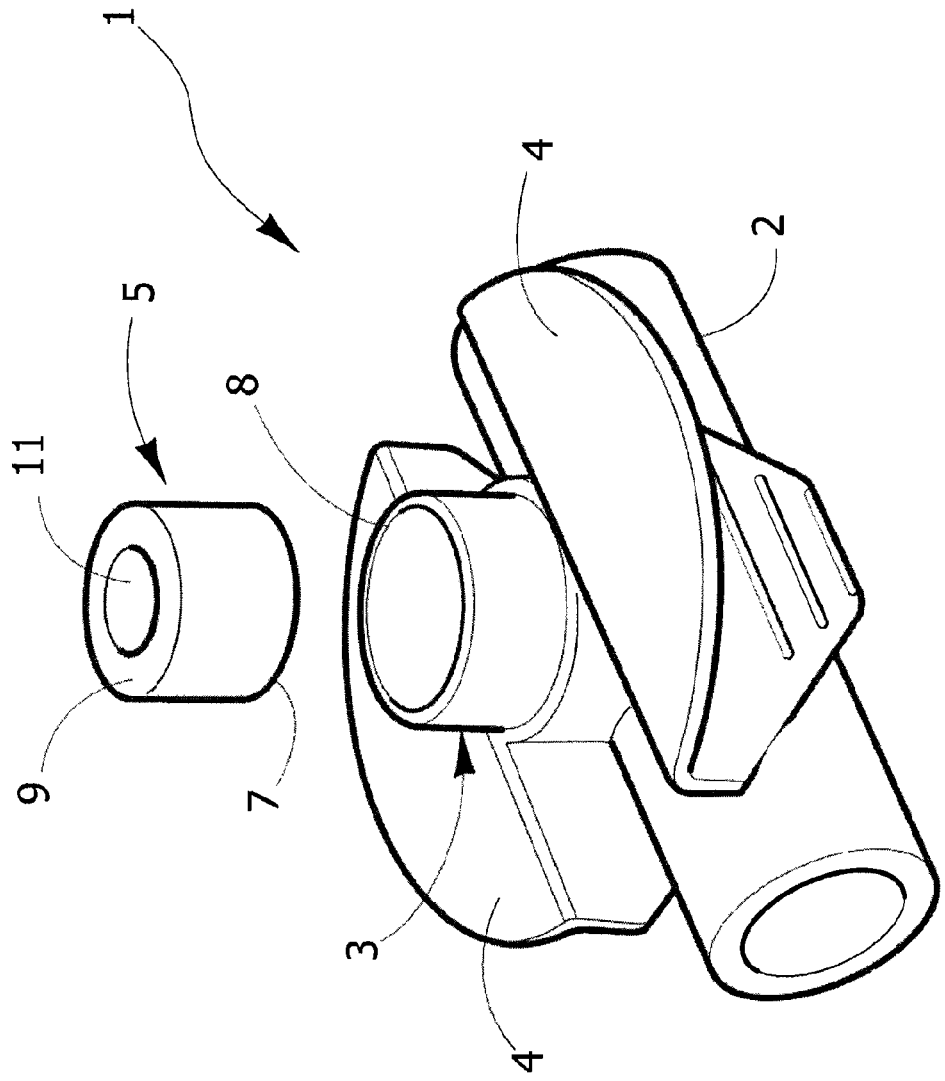
FIG. 2 is an exploded view of the embodiment of FIG. 1, which shows the flow component prior to its assembly.

With reference initially to FIGS. 1 to 3, designated as a whole by 1 is a flow component according to the invention, applicable to a medical infusion/transfusion line and consisting of a so-called T-shaped or cross-shaped needle point. The flow component 1 is formed by a tubular body that basically comprises a main duct 2, designed in use to be traversed by a flow of a primary liquid, and a side tubular inlet connector 3 directed perpendicularly, i.e., radially with respect to the duct 2, in a substantially median area of the latter, for introduction of a secondary liquid into it. A pair of gripping and protection tabs 4 project from the outer surface of the duct 2 on opposite sides with respect to the inlet connector 3.

Housed in a fluid-tight way within the inlet connector 3 is an elastic sealing element 5 having a generally cylindrical shape, typically made of a soft elastomeric material, such as silicone rubber and the like. Said elastic sealing element 5 is blocked and gripped axially at its ends between an internal axial arrest 6, defined by an annular flange of the connector 3, on which the internal end 7 of the elastic element 5 rests, and an axially external arrest constituted by the annular end edge 8 of the connector 3, bent against the external end 9 of the elastic element 5. Since the body of the flow component 1 is typically formed by just one piece of moulded plastic material, the annular edge 8 is bent back against the external end 9 of the elastic element 5, following upon its introduction within the inlet connector 3 in the way represented in FIG. 2, by means of hot plastic deformation.

According to the peculiar characteristic of the invention, the elastic sealing element 3 has, instead of a uniform axial thickness as in the case of the known art, a thinned-out central diaphragm 10 centred on its axis.

In the case of the example illustrated, the diaphragm of small thickness 10, the radial dimension of which can for example be comprised between ½ and ⅓ of the overall radial dimension of the elastic element 5, is delimited by a pair of opposed axial cavities 11, 12, which extend, respectively, from the external end 9 and from the internal end 7 of the body 5. Both of the cavities 11, 12 conveniently have a conical surface converging towards the diaphragm of small thickness 10.

This arrangement renders the elastic sealing element 5 reversible, in the sense that it can be mounted within the inlet connector 3 indifferently in the position represented in FIGS. 2 and 3, or in a position turned over through 180°.

It should, however, be pointed out that the diaphragm of small thickness 10 could also be defined by just the cavity 11, and in this case it would have an axial thickness evidently greater than what is represented in FIG. 3, or else also in an asymmetrical position, closer to the internal end 7 of the elastic element 5, and in this case the cavity 11 would have a greater depth.

In the configuration represented in FIG. 3, the dimensional parameters of the elastic sealing element 5 can, for example, be the following:

axial length: approximately 6.2 mm;
diametral width: approximately 7.6 mm;
axial length of the cavities 11, 12: approximately 2.5 mm;
maximum width of the cavities 11, 12: approximately 3.6 mm;
minimum width of the cavities 11, 12, i.e., diametral dimension of the diaphragm 10: approximately 2 mm;
axial thickness of the diaphragm 10: approximately 1.2 mm.

According to another peculiar aspect of the invention, the axially external arrest defined by the annular bent-back edge 8 of the inlet connector 3 is set, against the external end 9 of the elastic element 5, in the immediate radial proximity of the cavity 11. In this way, the conical wall of the cavity 11 converging towards the diaphragm 10 extends, practically without solution of continuity, on the prolongation of the bent-back edge 8.

In use, the diaphragm of small thickness 10 is designed to be traversed by the needle of a conventional syringe for introduction, through the inlet connector 3, of the secondary liquid within the main duct 2 traversed by the primary liquid. Thanks to the conformation described above the needle of the syringe will traverse, instead of the entire axial thickness of the elastic element 5 as in the case of conventional flow components, only the small thickness of the diaphragm 10, thus reducing considerably the effort that the operator must apply on the needle for perforation. Furthermore, the conical-surface conformation of the cavity 11, and the position of the bent-back edge of arrest 8 in the proximity of the cavity 11, facilitate the proper centering of the needle against the diaphragm 11, considerably reducing the risk of an erroneous insertion.

The variant of the flow component according to the invention illustrated schematically and partially in FIG. 4 (in which parts that are identical or similar to the ones previously described are designated by the same reference numbers) relates to a so-called valve Luer connector, i.e., to the case where the inlet connector 3 with the elastic sealing element 5 is designed to be used with a fluid introducer without needle, of the male-Luer-cone type. In this case, the cavity 11 that delimits the diaphragm of small thickness 10 has a female-Luer-cone configuration, and the diaphragm 10 is formed centrally with a pre-slit 13. Said pre-slit 13 is normally closed so as to seal the inlet connector 3 in a fluid-tight way, and is openable as a result of the introduction and traversal of the diaphragm 10 by the male-Luer fluid introducer.

In this type of application, the cavity 11 typically has a depth greater than the one described with reference to FIGS. 1 to 3 so that the diaphragm 10 is set asymmetrically, i.e., closer to the axially internal end 7 of the elastic element 5. The second cavity, set between the diaphragm 10 and the internal end 7 of the elastic element 5 may in said case be absent or, if present, have a limited axial dimension, as designated by 12 in FIG. 4.

Of course, the details of construction and the embodiments may vary widely with respect to what has been described and illustrated herein, without thereby departing from the scope of the present invention, as defined in the ensuing claims.

What is claimed is:

1. A flow component for medical infusion/transfusion lines, comprising:

a tubular body having a side inlet connector configured to allow a fluid introducer to be inserted therein, said inlet connector housing in a fluid-tight way an elastic sealing element having a generally cylindrical shape, axially blocked at its ends between two annular arrests, one of said annular arrests axially internal of said inlet connector and another of said annular arrests axially external of said inlet connector;

said elastic sealing element having an axial cavity on a side of the external annular arrest of the inlet connector, said axial cavity defining a diaphragm of small thickness for traversal by said fluid introducer;

said cavity of said elastic sealing element having a conical side surface converging toward said diaphragm of small thickness;

said elastic sealing element having a second axial cavity on a side of said internal annular arrest of the inlet connector, said second axial cavity having a conical side surface converging toward said diaphragm of small thickness;

said diaphragm situated in a median position of said elastic element between said cavity and said second cavity; and wherein said axially external annular arrest is formed by an annular end edge of said inlet connector formed monolithically relative to a remainder of said inlet connector, said inlet connector having an interior surface extending along an outer surface of said sealing element, said interior surface curving upwardly away from said tubular body over a top of said sealing element and downwardly to said external annular arrest to form a space between said interior surface and a top side of said sealing element, and said external annular arrest located in an immediate radial proximity of said cavity of the elastic sealing element and having an outer surface flush with an interior surface of said sealing element bounding said axial cavity to facilitate a centering of the fluid introducer in said diaphragm.

2. The flow component according to claim 1, wherein said diaphragm of small thickness is configured to be perforated by a syringe needle.

3. The flow component according to claim 1, wherein said diaphragm of small thickness has an axial pre-slit openable by a needleless syringe.

4. The flow component according to claim 1, wherein said axial cavity is shaped as a female Luer connector.

5. The flow component according to claim 1, wherein said elastic sealing element is made of soft elastomeric material.

6. A flow component for medical infusion/transfusion lines, comprising:

a tubular body having a side inlet connector configured to allow a fluid introducer to be inserted therein, said inlet connector housing in a fluid-tight way an elastic sealing element having a generally cylindrical shape, said sealing element axially blocked at its ends between two annular arrests, one of said annular arrests axially internal of said inlet connector and another of said annular arrests axially external of said inlet connector;

said axially external annular arrest formed by an annular end edge of said inlet connector formed monolithically relative to a remainder of said inlet connector, said inlet connector having an interior surface extending along an outer surface of said sealing element, said interior surface curving upwardly away from said tubular body over a top of said sealing element and downwardly to said external annular arrest, wherein a shape of an exterior surface of said inlet connector facilitates a centering of the fluid introducer in said diaphragm;

said elastic sealing element having an axial cavity on a side of the external annular arrest of the inlet connector, said axial cavity defining a diaphragm having a thickness configured for traversal by said fluid introducer;

said cavity of said elastic sealing element having a conical side surface converging toward said diaphragm;

said external annular arrest having an outer surface flush with an interior surface of said sealing element bounding said axial cavity to facilitate said centering of the fluid introducer in said diaphragm;

said elastic sealing element having a second axial cavity on a side of said internal annular arrest of the inlet connector, said second axial cavity having a conical side surface converging toward said diaphragm; and said diaphragm situated in a median position of said elastic element between said first cavity and said second cavity.

7. A flow component for medical infusion/transfusion lines, comprising:

a tubular body having a side inlet connector configured to allow a fluid introducer to be inserted therein, said inlet connector housing in a fluid-tight way an elastic sealing element having a generally cylindrical shape, said sealing element axially blocked at its ends between two annular arrests, one of said annular arrests axially internal of said inlet connector and another of said annular arrests axially external of said inlet connector;

said axially external annular arrest formed by an annular end edge of said inlet connector, said inlet connector having an interior surface extending along an outer surface of said sealing element, said interior surface curving upwardly away from said tubular body over a top of said sealing element and downwardly to said external annular arrest, wherein a shape of an exterior surface of said inlet connector facilitates a centering of the fluid introducer in said diaphragm;

said elastic sealing element having an axial cavity on a side of the external annular arrest of the inlet connector, said axial cavity defining a diaphragm having a thickness configured for traversal by said fluid introducer;

said cavity of said elastic sealing element having a conical side surface converging toward said diaphragm;

said external annular arrest having an outer surface flush with an interior surface of said sealing element bounding said axial cavity to facilitate said centering of the fluid introducer in said diaphragm;

said elastic sealing element having a second axial cavity on a side of said internal annular arrest of the inlet connector, said second axial cavity having a conical side surface converging toward said diaphragm; and said diaphragm situated in a median position of said elastic element between said cavity and said second cavity.

* * * * *